US008238996B2

(12) United States Patent
Burnes et al.

(10) Patent No.: US 8,238,996 B2
(45) Date of Patent: Aug. 7, 2012

(54) ELECTRODE ARRAY

(75) Inventors: Lee Burnes, Franklin, MA (US); Scott Coggins, Palmer, MA (US); Dawn Moore, Sturbridge, MA (US); Mark Tauer, Belchertown, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 911 days.

(21) Appl. No.: 11/951,086

(22) Filed: Dec. 5, 2007

(65) Prior Publication Data

US 2008/0154110 A1    Jun. 26, 2008

Related U.S. Application Data

(60) Provisional application No. 60/872,813, filed on Dec. 5, 2006.

(51) Int. Cl.
*A61B 5/0408* (2006.01)
(52) U.S. Cl. ......... 600/382; 600/386; 600/390; 600/393
(58) Field of Classification Search .................. 600/382, 600/388, 389, 393
See application file for complete search history.

(56) References Cited

U.S. PATENT DOCUMENTS

| | | |
|---|---|---|
| 3,752,151 A | 8/1973 | Robichaud |
| 3,805,769 A | 4/1974 | Sessions |
| 3,828,766 A | 8/1974 | Krasnow |
| 3,868,946 A | 3/1975 | Hurley |
| 3,888,240 A | 6/1975 | Reinhold, Jr. et al. |
| 3,901,218 A | 8/1975 | Buchalter |
| 3,998,213 A | 12/1976 | Price |
| 4,027,664 A | 6/1977 | Heavner, Jr. et al. |
| 4,034,854 A | 7/1977 | Bevilacqua |
| 4,077,397 A | 3/1978 | Ellis et al. |
| 4,353,372 A | 10/1982 | Ayer |
| 4,365,634 A | 12/1982 | Bare et al. |
| 4,498,480 A | 2/1985 | Mortensen |
| 4,729,377 A | 3/1988 | Granek et al. |
| 4,763,660 A | 8/1988 | Kroll et al. |

(Continued)

FOREIGN PATENT DOCUMENTS

DE    102004032410    1/2006

(Continued)

OTHER PUBLICATIONS

International Search Report EP07253850 dated Dec. 21, 2007.

(Continued)

*Primary Examiner* — Lee Cohen
*Assistant Examiner* — Erin M Cardinal
(74) *Attorney, Agent, or Firm* — Lisa E. Winsor, Esq.

(57) ABSTRACT

A sensor array apparatus for monitoring medical signals includes a flexible substrate adapted for positioning relative to the torso of a patient. The flexible substrate includes a central segment defining a central axis and is adapted to generally conform to an area extending along the sternum of a patient. The flexible substrate further includes an upper segment extending traversal across the central segment and adapted to generally conform to the chest area of a patient and a lower segment extending traversal across the central segment and adapted to generally conform to the abdominal area of the patient. The apparatus further includes a medical electrode disposed on at least one of the segments and a connector in electrical communication with the medical electrode and adapted to connect to an electronic monitoring system.

22 Claims, 6 Drawing Sheets

U.S. PATENT DOCUMENTS

| | | | |
|---|---|---|---|
| 4,781,200 A | 11/1988 | Baker | |
| 4,785,822 A | 11/1988 | Wallace | |
| 4,815,964 A | 3/1989 | Cohen et al. | |
| 4,909,260 A | 3/1990 | Salem et al. | |
| 4,947,846 A | 8/1990 | Kitagawa et al. | |
| 4,957,109 A | 9/1990 | Groeger et al. | |
| 5,224,479 A | 7/1993 | Sekine | |
| 5,263,481 A | 11/1993 | Axelgaard | |
| 5,341,806 A | 8/1994 | Gadsby et al. | |
| 5,353,793 A | 10/1994 | Bornn | |
| 5,370,116 A | 12/1994 | Rollman et al. | |
| 5,405,269 A | 4/1995 | Stupecky | |
| 5,445,149 A * | 8/1995 | Rotolo et al. | 600/382 |
| 5,507,290 A | 4/1996 | Kelly et al. | |
| 5,511,553 A | 4/1996 | Segalowitz | |
| 5,546,950 A | 8/1996 | Schoeckert et al. | |
| 5,582,180 A | 12/1996 | Manset et al. | |
| 5,622,168 A | 4/1997 | Keusch et al. | |
| 5,685,303 A | 11/1997 | Rollman et al. | |
| 5,704,351 A | 1/1998 | Mortara et al. | |
| 5,724,984 A | 3/1998 | Arnold et al. | |
| 5,813,979 A | 9/1998 | Wolfer | |
| 5,865,740 A | 2/1999 | Kelly et al. | |
| 5,865,741 A | 2/1999 | Kelly et al. | |
| 5,913,834 A | 6/1999 | Francais | |
| 5,916,159 A | 6/1999 | Kelly et al. | |
| 5,938,597 A | 8/1999 | Stratbucker | |
| 6,006,125 A | 12/1999 | Kelly et al. | |
| 6,032,064 A | 2/2000 | Devlin et al. | |
| 6,055,448 A | 4/2000 | Anderson et al. | |
| 6,066,093 A | 5/2000 | Kelly et al. | |
| 6,115,623 A | 9/2000 | McFee | |
| 6,122,536 A | 9/2000 | Sun et al. | |
| 6,122,544 A | 9/2000 | Organ | |
| 6,157,851 A | 12/2000 | Kelly et al. | |
| 6,219,568 B1 | 4/2001 | Kelly et al. | |
| 6,219,569 B1 | 4/2001 | Kelly et al. | |
| 6,232,366 B1 | 5/2001 | Wang et al. | |
| 6,240,323 B1 | 5/2001 | Calenzo, Sr. et al. | |
| 6,304,783 B1 | 10/2001 | Lyster et al. | |
| 6,339,720 B1 | 1/2002 | Anzellini et al. | |
| 6,360,119 B1 | 3/2002 | Roberts | |
| 6,400,977 B1 | 6/2002 | Kelly et al. | |
| 6,415,169 B1 * | 7/2002 | Kornrumpf et al. | 600/382 |
| 6,453,186 B1 | 9/2002 | Lovejoy et al. | |
| 6,456,872 B1 | 9/2002 | Faisandier | |
| 6,553,246 B1 | 4/2003 | Wenger | |
| 6,553,250 B2 | 4/2003 | Rantala | |
| 6,564,079 B1 | 5/2003 | Cory et al. | |
| 6,611,705 B2 | 8/2003 | Hopman et al. | |
| 6,623,312 B2 | 9/2003 | Merry et al. | |
| 6,636,754 B1 | 10/2003 | Baura et al. | |
| 6,647,286 B1 | 11/2003 | Kato et al. | |
| 6,654,626 B2 | 11/2003 | Devlin et al. | |
| 6,748,797 B2 | 6/2004 | Breed et al. | |
| 6,751,493 B2 | 6/2004 | Wenger | |
| 6,768,921 B2 | 7/2004 | Organ et al. | |
| 6,816,744 B2 | 11/2004 | Garfield et al. | |
| 6,847,836 B1 | 1/2005 | Sujdak | |
| 6,970,731 B1 | 11/2005 | Jayaraman et al. | |
| 6,973,341 B2 | 12/2005 | Watson | |
| 6,973,343 B2 | 12/2005 | Wenger | |
| 6,980,852 B2 | 12/2005 | Jersey-Willuhn et al. | |
| 7,104,801 B1 | 9/2006 | Brodnick et al. | |
| 7,150,655 B2 | 12/2006 | Mastrototaro et al. | |
| 7,169,107 B2 | 1/2007 | Jersey-Willuhn et al. | |
| 7,184,820 B2 | 2/2007 | Jersey-Willuhn et al. | |
| 7,197,357 B2 | 3/2007 | Istvan et al. | |
| 7,272,428 B2 | 9/2007 | Hopman et al. | |
| 7,319,895 B2 | 1/2008 | Klefstad-Sillonville et al. | |
| 7,333,850 B2 | 2/2008 | Marossero et al. | |
| 2002/0133069 A1 | 9/2002 | Roberts | |
| 2002/0188216 A1 | 12/2002 | Kayyali et al. | |
| 2004/0073127 A1 | 4/2004 | Istvan et al. | |
| 2004/0127802 A1 | 7/2004 | Istvan et al. | |
| 2004/0176674 A1 | 9/2004 | Nazeri | |
| 2005/0177052 A1 | 8/2005 | Istvan et al. | |
| 2005/0203349 A1 | 9/2005 | Nanikashvili | |
| 2006/0073728 A1 | 4/2006 | Zaiken et al. | |
| 2006/0117805 A1 | 6/2006 | Valentine et al. | |
| 2007/0038057 A1 | 2/2007 | Nam et al. | |
| 2007/0260133 A1 | 11/2007 | Meyer | |
| 2008/0143080 A1 | 6/2008 | Burr | |

FOREIGN PATENT DOCUMENTS

| | | |
|---|---|---|
| EP | 0766946 | 4/1997 |
| EP | 1050269 | 11/2000 |

OTHER PUBLICATIONS

Andreas Boos et al.; "A New Lightweight Fetal Telemetry System"; Dec. 1995; Hewlett-Packard Journal; pp. 82-93.

International Search Report EP07 25 1765 dated Mar. 31, 2008.

International Search Report EP07 25 4691 dated Mar. 25, 2008.

International Search Report EP08 16 4409 dated Jan. 27, 2009.

* cited by examiner

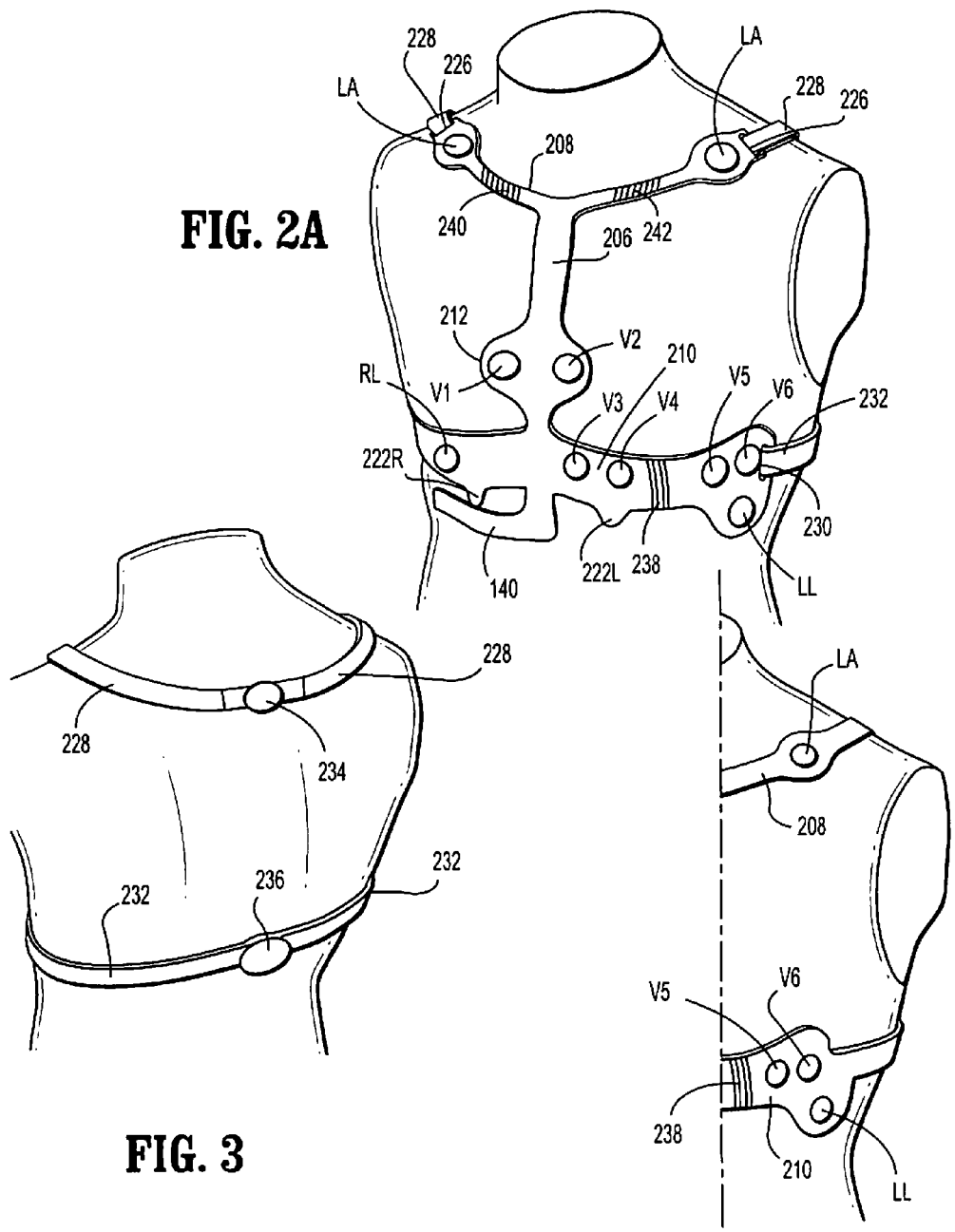
FIG. 2A
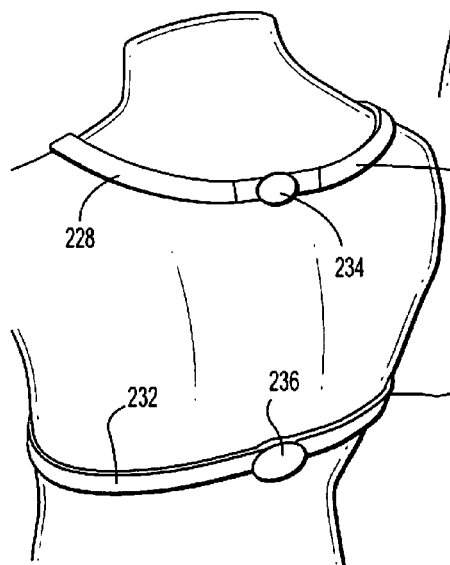
FIG. 3
FIG. 2B

ELECTRODE ARRAY

CROSS-REFERENCE TO RELATED APPLICATIONS

This application claims priority to provisional patent application entitled "ELECTRODE ARRAY" filed in the United States Patent and Trademark Office on Dec. 5, 2006 and assigned Ser. No. 60/872,813, the entire contents of which disclosure is hereby incorporated by reference herein.

BACKGROUND

1. Technical Field

The present disclosure relates to a sensor array apparatus and, more particularly, relates to a disposable sensor array apparatus adapted for applying an array of electrodes to the body surface of patients during use with an ECG monitor.

2. Description of Related Art

Electrocardiograph (ECG) monitors are widely used to obtain biopotential signals containing information indicative of the electrical activity associated with the heart and pulmonary system. To obtain information, biopotential signal electrodes are applied to the skin of a patient in various locations depending on the information sought by the clinician. Electrodes are often covered or coated by a conductive gel which serves as an electrochemical coupling agent and enhances the ability of the electrode to adhere to a patient's skin.

ECG electrodes may be placed in various lead configurations. The most prevalent configurations are a 3-lead, 5-lead or 12-lead configuration. In conventional electrocardiography, electrodes are positioned on the patient's skin at locations established by a medical protocol. For a 3-lead configuration, three electrodes are placed on the body. One electrode is placed adjacent each clavicle bone on the upper chest and the third is placed on the patient's lower left abdomen. For a 5-lead configuration, five electrodes are placed on the body. In addition to the electrodes used for the 3-lead, a fourth electrode is placed adjacent the sternum and a fifth is placed on the patient's lower right abdomen. For a 12-lead configuration, ten leads are placed on the patient's body. Four electrodes are placed on the patient to represent his/her limbs including, the left arm electrode (LA), the right arm electrode (RA), the left leg electrode (LL), and the right leg electrode (RL). Six chest electrodes (V1-V6) are placed on the patient's chest at various locations near the heart. Three standard leads are provided by measurements taken from the right arm to left arm (Lead I), from the right arm to the left leg (Lead II) and from the left arm to the left leg (Lead III). Three augmented leads are provided by measurements taken from RA, RL and LL to LA (AVL), from LA, LL and RL to RA (AVR) and from RA and LA to LL and RL (AVF). The ten electrodes result in twelve measurements, which consist of Leads I, II, III, AVR, AVL, AVF, and V1-V6, with RL typically used as the ground electrode.

Electrodes, after proper positioning on the patient, are connected to an ECG monitor, recorder or diagnostic device by an ECG lead set. One end of the ECG lead set attaches to each electrode (or the electrodes may be integrated into the ECG lead set) and receives biopotential signals from the body. The second end of the ECG lead set connects to an ECG monitor and supplies the biopotential signals to an ECG monitor. This connection to the ECG monitor can be done wirelessly such as in Medical Telemetry or directly using a traditional cable harness. The signals are processed by the ECG monitor for use and analysis by medical personnel.

The quality of the information obtained by each electrode is determined by the connection between the electrode and patient skin, the placement of the electrode on the patient relative to the signal source and consistent placement of electrodes relative to each other. It would thus be desirable if accurate placement of the electrodes could be ensured through a releasably applicable apparatus having the ability to conform to a variety of body surfaces.

SUMMARY

Accordingly, the present disclosure is directed to an electrode sensor array apparatus useful in a diagnostic application, e.g., electrocardiogram (ECG), to collect clinical data such as monitoring of electrical activity associated with the heart and pulmonary system. The sensor array apparatus facilitates accurate and consistent electrode placement on the patient and ensures accurate and consistent placement of electrodes relative to each other during successive uses. The sensor array apparatus is adapted to conform to body types of various sizes, and, preferably, at least partially spans a body portion, e.g., the torso of the subject. The sensor array apparatus may be releasably secured to the body portion with various means including belts, straps, etc, and, as such, may permit some range of transportability of the patient during the procedure.

In an embodiment, a sensor array apparatus for monitoring biopotential signals includes a flexible substrate adapted, e.g., to generally conform to the torso of a patient. The flexible substrate includes a central segment defining a central axis and adapted to generally conform, e.g., to an area extending along the sternum of the patient. The flexible substrate further includes an upper segment extending to the central segment and adapted to generally conform to the chest area of the patient and a lower segment extending to the central segment and adapted to generally conform, e.g., to the abdominal area of the patient. A medical electrode is disposed on at least one of the segments and a connector in electrical communication with the medical electrode is adapted to connect to an electronic monitoring system.

In another embodiment of the present disclosure, a sensor array apparatus for monitoring medical signals includes a flexible substrate adapted for positioning relative to the torso of a patient. The flexible substrate includes a central segment arranged about a central axis and adapted to generally conform to an area extending along the sternum of a patient. The flexible substrate further includes an upper segment extending bilaterally outwardly from the central segment and adapted to generally conform to the chest area of a patient and a lower segment extending bilaterally outwardly from the central segment and adapted to generally conform to the abdominal area of the patient. At least one of the upper segment and the lower segment is adapted to releasably couple to at least one fastener strap adapted to secure the flexible substrate to the torso of the patient. A medical electrode is disposed on at least one of the segments and a connector in electrical communication with the medical electrode is adapted to connect to an electronic monitoring system.

In yet another embodiment, a sensor array apparatus for monitoring medical signals includes a flexible substrate adapted for positioning relative to the torso of a patient. The flexible substrate includes at least one substantially horizontal segment and at least one substantially vertical segment. At least one of the substantially horizontal segment and the substantially vertical segment are adapted to releasably couple to at least one fastener strap adapted to secure the flexible substrate to the torso of the patient. A medical electrode is disposed on at least one of the segments and a connector in electrical communication with the medical electrode is adapted to connect to an electronic monitoring system.

BRIEF DESCRIPTION OF THE DRAWINGS

Various embodiments of the sensor array apparatus are described herein with reference to the drawings wherein:

FIG. 2A is a front perspective view of the sensor array apparatus of FIG. 1 applied to the torso of a patient;

FIG. 2B is a cut-away front perspective view of a sensor array apparatus applied generally to the left shoulder area of a patient according to an embodiment of the present disclosure;

FIG. 3 is a rear perspective view of the sensor array apparatus of FIG. 1 applied to the torso of a patient.

DETAILED DESCRIPTION

Figure 1:
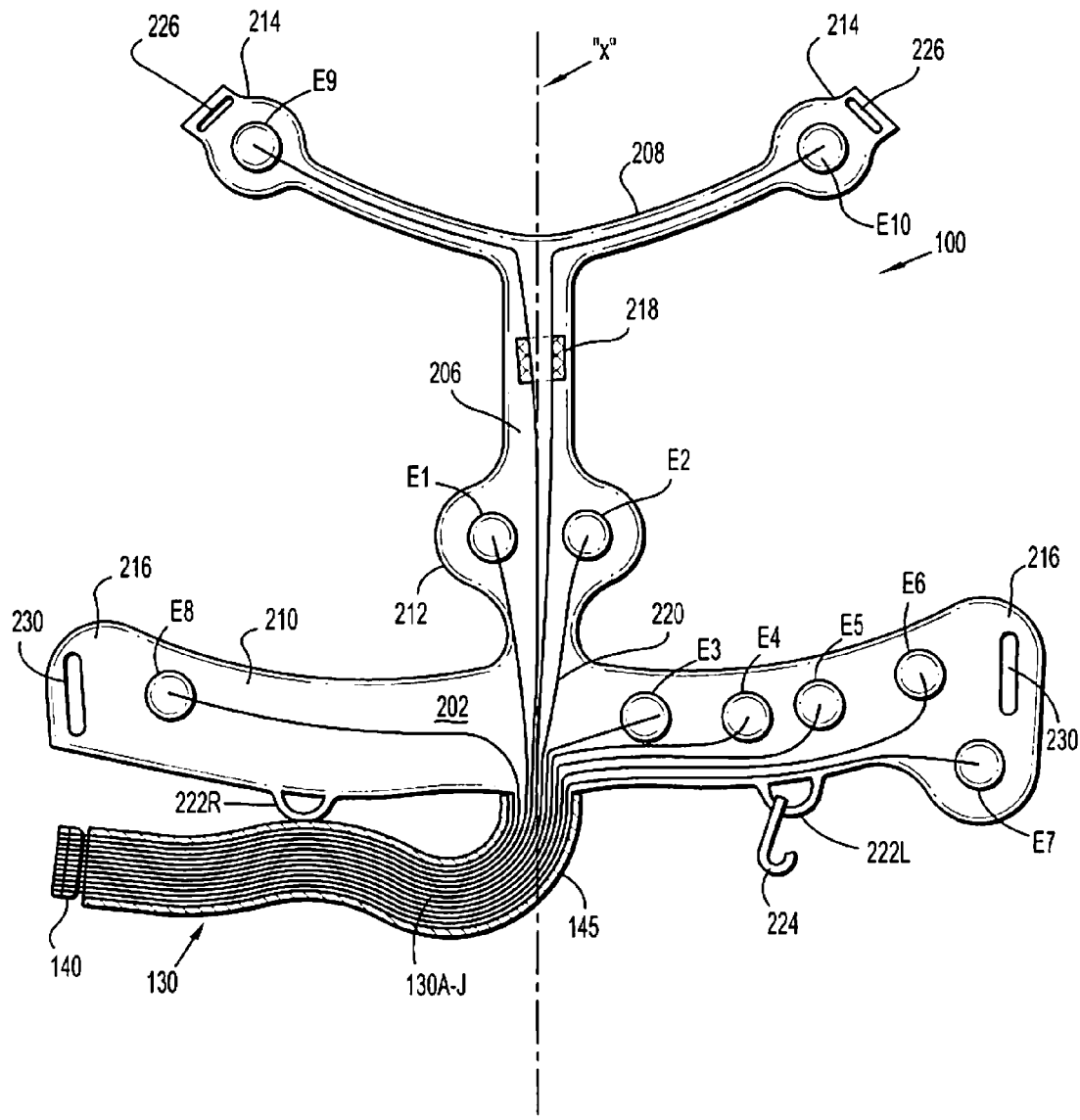
FIG. 1 is a view of the sensor array apparatus for monitoring electrical activity associated with the heart and pulmonary system illustrating the flexible substrate having central, upper and lower segments.

Embodiments of the presently disclosed sensor array apparatus will now be described in detail with reference to the drawing wherein like reference numerals identify similar or identical elements throughout the several views.

In general, the sensor array apparatus of the present disclosure includes medical electrodes to measure or collect data concerning electrical activity generated within the body. The type of electrode selected, and the placement of the electrode on the body, will determine the type of electrical activity measured. Any type of electrode known in the art may be used with the embodiments of the sensor array apparatuses described herein. The electronic system may be any system known in the art capable of receiving electronic signals. In embodiments, the sensor array apparatus is a component of an electronic system used in the non-invasive monitoring of electrical activity associated with the heart and pulmonary system. Other applications of the sensor array apparatus are also envisioned.

Referring now to FIG. 1, an embodiment of a sensor array apparatus in accordance with the present disclosure will be discussed. In FIG. 1, sensor array apparatus 100 is illustrated for use in connection with an ECG monitoring procedure. Medical electrodes of sensor array apparatus 100 are configured to be in contact with the torso of the patient and in electrical communication with an electronic system (not shown). The electronic system receives and processes electrical impulses from sensor array apparatus 100 containing electrocardiographic information for use by the user/clinician.

With continued reference to FIG. 1, sensor array apparatus 100 includes flexible substrate 202, medical electrodes E1-E10 disposed on the substrate 202, and connector 204. Flexible substrate 202 is constructed of a flexible material capable of generally conforming to the topography of a skin surface. Flexible substrate 202 may be formed from a non-conducting material which is sufficiently flexible and sufficiently strong to maintain its position on the patient and the relative positioning of chest electrodes. Suitable materials include Mylar™ or any other biaxially-oriented polyethylene terephthalate polyester films, Teslin™ or any other polyolefin silica blend, natural woven fibers, synthetic non-woven material or paper.

Flexible substrate 202 includes central segment 206 defining a central axis "x", and upper and lower segments 208, 210 at respective ends of the central segment 206. Central segment 206 is generally linear extending along central axis "x" and includes a bulbous intermediate segment 212. Central segment 206 is dimensioned to extend along the midline of the torso from the chest area toward the navel area. Upper segment 208 may have an arcuate character or may be linear and extends to traverse the central axis "x". Upper segment 208 may be arranged to at least partially circumscribe the neck area when applied to the patient whereby remote ends 214 of the upper segment 208 extend about respective shoulder areas. Lower segment 210 may be arcuate in character or may be linear. Lower segment 210 also traverses the central axis "x". Lower segment 208 may be arranged to at least partially traverse the abdominal area adjacent the ribs whereby remote ends 216 of the lower segment are positioned adjacent respective sides the subject.

Central segment 206 may include a placement marker configured to facilitate accurate placement of the flexible substrate 202 on the patient's torso. In one embodiment, integrated electrode E1 on flexible substrate 202 may serve as a placement marker. With this arrangement, electrode E1 may be placed over or adjacent an easily recognizable portion of the anatomy, e.g., a portion of the sternum, to ensure proper placement of flexible substrate 202 and, thus, electrodes E1-E10 on the patient's skin surface. The visible surface of flexible substrate 202 may incorporate color-coded and/or nomenclature visual indicia (represented schematically as reference numeral 218) for additional guidance in proper placement of flexible substrate 202. The visual indicia 218 may correspond for positioning on any torso landmark.

In FIG. 1, flexible substrate 202, including central segment 206 and upper and lower segments 208, 210, is generally arranged in a symmetrical arrangement with respect to the central axis "x" to divide the flexible substrate 202 into two half sections. However, it is noted that flexible substrate 202 does not need to be symmetrical about an axis.

Referring to FIG. 1, in conjunction with FIG. 2A, central, upper and lower segments 206, 208, 210 include at least one electrode E1-E10 in electrical communication with connector 140 which is adapted to connect to an electronic system. Any means for mounting/integrating electrodes E1-E10 to flexible substrate 202 are envisioned. As to be appreciated, flexible substrate 202 may include a dielectric layer (not shown) to minimize undesired external electrical noise or interference with electrodes E1-E10. In a twelve lead ECG application, one single electrode E1, E2 may be disposed on intermediate bulbous segment 212 of central segment 206 on each side of central axis "x". Six electrodes E3-E8 may be disposed on lower segment 210 with electrodes E3-E7 being disposed on one side of central axis "x" and one electrode E8 on the other side of the central axis "x". E9, E10 is disposed on upper segment 208 of flexible substrate 202 adjacent each remote end. E9 and E10 are the RA, RL electrode leads in the twelve lead ECG set. E7 and E8 are the LL, RL leads, respectively. Electrodes E1-E6 are the V or chest electrode leads. Preferably, when applied to the subject electrodes, E1, E2 are positioned in the fourth intercostal space to the right and left respectively of the sternum. E4 is positioned in the fifth intercostal space in the mid-clavicular line, E3 is positioned between E4 and E2, E6 is positioned in the fifth intercostal space in the mid axillary line E5 is positioned between E4 and E6.

Electrodes E1-E10 are each a predetermined distance relative to central axis "x". In FIG. 1, the respective distances between central axis "x" and electrode pair E9, E10 and electrode pair E1, E2 may be substantially equivalent. Similarly, the respective distances between central axis "x" and electrode pair E6, E8 may be substantially equivalent. The distances between central axis "x" and electrodes E3-E7 are predetermined, such that each electrode E3-E7 is spaced relative to each other in a specific configuration suitable for ECG monitoring of a human subject. Thus, when the placement marker, e.g., electrode E1, is properly placed on the patient's torso, the relative distances of the corresponding electrodes E1-E10 remain proportionally substantially equivalent with respect to central axis "x" and with respect to the remaining corresponding electrodes. Thus, this arrangement provides for accurate and consistent electrode placement on the curved skin surface, which thereby enhances the reliability and accuracy of the clinical data acquired during the monitoring process. An unintegrated electrode arrangement of flexible substrate 202 is also envisioned.

In systems or applications, electrodes E1-E10 may be either bipolar or unipolar (monopolar) electrodes. In a unipolar system, electrodes E1-E10 measure electrical activity relative to a single designated electrode (not shown). Electrical activity at each electrode E1-E10 is measured with respect to the reference electrode. In a bipolar system, electrodes E1-E10 measure electrical activity relative to any two or more of electrodes E1-E10, i.e., multiple reference electrodes may be utilized.

With continued reference to FIG. 1, sensor array apparatus 100 includes a lead set 130. Lead set 130 includes a plurality of lead wires 130A-J at least partially surrounded by a sheath 145. Sheath 145 may protect lead wires 130A-J from physical damage or may shield lead wires 130A-J from electrical interference or noise. The sheath 145 portion of the sensor array apparatus 100 may vary in length, typically about two to ten feet.

The lead wire ends remote from to the monitor/recorder 130 may connect to one or more electrode connectors (not shown) via, e.g., snap connectors, locking slot connectors, keyhole connectors, dumbbell connectors, etc., configured to connect to electrodes E1-E10. Alternately, these ends of lead wires 130A-J may couple to at least one electrode E1-E10 pre-wired to an individual lead wire 130A-J or lead wires 130A-J may be integrated into electrodes 130A-J. One or more electrodes E1-E10 may be coupled to an end of each individual lead wire 130A-J or electrodes E1-E10 may be formed from an individual lead wire 130A-J. Irrespective of the electrode configuration, (e.g., electrode connectors, pre-wired and/or integrated electrodes), in use the electrodes are connected to lead set 130, disposed on the patient and configured to receive biopotential signals.

In FIG. 1, sheath 145 terminates at lower segment 210 of flexible substrate 202. However, sheath 145 may extend to any area of flexible substrate 202 including central segment 206, upper segment 208 or may encompass an entire section or area thereof. At least a portion of lead wires 130A-J may extend distally from sheath 145 to be integrally defined on flexible substrate 202 as, e.g., conductive traces 220, to place electrodes E1-E10 and connector 140 in electrical communication. As to be appreciated, conductive traces 220 can be printed directly onto flexible substrate 202 if the flexible substrate 202 is a dielectric. Alternatively, conductive traces 220 may be printed on a separate carrier sheet if flexible substrate 202 is not a dielectric material. Various methods of printing conductive traces include silk screen printing, photoengraving, chemical etching, laser etching or mask electrode. Stretchable conductors, such as stretchable gold strip conductors, may be used with a flexible substrate that exhibits elongation properties as will be discussed.

Connector 140 is coupled to the lead set end proximal to the monitor/recorder and configured for electrical communication with an electronic system (not shown) through a trunk cable or an adapter (not shown). In embodiments, connector 140 provides at least ten connectors (not shown) suitable for connection with a 3/5 lead trunk cable (not shown) enabling ECG monitoring or a 12 lead trunk cable (not shown) enabling ECG monitoring and/or diagnostic testing. It should be understood that the 3/5 lead trunk cable/adapter is interchangeable with the 12 lead trunk cable/adapter with respect to connector 140, enabling quick and easy switching between 3 lead, 5 lead, and 12 lead operation of an ECG monitoring system. As would be understood by those skilled in the art, in a 12 lead monitoring or diagnostic arrangement, all ten connections are in electric communication with the diagnostic trunk cable/adapter. In a 3 lead and/or 5 lead arrangement, 3 or 5 connections are in electrical communication with the monitoring trunk cable/adapter, i.e., the remaining unused connections are dead. In this manner, connector 140 is adaptable for 3 lead, 5 lead, and 12 lead configurations. The trunk cables/adapters may include an antimicrobial coating to maximize hygienic cleanliness, thereby preserving the cable and enhancing its reusability. A phone chord or helical design of the trunk cable/adapter is also envisioned to provide enhanced flexibility and/or maneuverability of the trunk cable during operation of sensor array apparatus 100.

Lead set 130 may be formed from a plurality of individual wires or from a suitable cable containing a plurality of wires, such as, for example, a multi-conductor shielded cable or ribbon cable. Sheath 145 may be the cable jacket or may be a separate tubular member at least partially surrounding a portion and/or length of the plurality of individual wires or cable. Sheath 145 may be integrated into cable connector 140 or may be formed from a suitable tubular member and coupled to the connector 140. Sheath 145 may consist of printing additional layer(s) of conductive traces above and below the ECG signal conducting traces with dielectric layers in between that are substantially wider than the group of ECG signal carriers. Alternatively, with a flexible circuit lead set (130) the dielectric layers above & below the ECG signal conducting traces could be coated with a flexible shielding material such as a silver epoxy paint. The entire substrate (202) could be similarly shielded.

Connection of lead set 130 to central segment 206 of flexible substrate 202 allows cable connector 140 to be placed on either side of the patient depending on which side of the patient the electronic system is located. Adhesive backed sliders or tabs 222R and 222L may be positioned on respective sides of lower segment 206, to secure lead set 130 to the right or left side of flexible substrate 202 and/or to prevent patient discomfort. Tabs 222R and 222L may incorporate gel material on each side of the tabs 222R and 222L to secure respectively to the patient and the lead set 130 to maintain a low profile while promoting patient comfort. As a further alternative, a clip 224 adapted to secure to lead set 130 may be provided.

In use of sensor array apparatus 100 as depicted in FIGS. 2-3, flexible substrate 202 is applied to the torso of a human subject. In arrangements, a portion of the sternum may be used as a reference point and flexible substrate 202 is positioned onto the torso such that the electrode E1 position is substantially aligned with the portion of the sternum or, alternatively, the visual indicia 218 may be aligned with the reference point (e.g., a body part or reference). Flexible substrate 202 is arranged with central segment 206 extending along the midline of the patient's chest (i.e., the vertical line extending up the chest and intersecting the sternum) and with upper segment 208 adjacent the upper chest portion and lower segment 210 adjacent the rib area. The electronic system is activated and data is collected by electrodes E1-E10. This procedure may be repeated several times if desired. With each application, a portion of the sternum may be used as a reference point for application of flexible substrate 202 thereby ensuring accurate and consistent placement of the electrodes for successive data acquisition procedures. Other locations on flexible substrate 202 for the placement marker are envisioned, e.g., the E2 position or between the E1 and E2 positions.

With reference now to FIGS. 1-3, upper segment 208 may include apertures 226 through each of remote ends 214 and coupled to two fastener straps 228 respectively. Lower segment 210 includes apertures 230 extending through remote ends 216 and configured to be coupled to two fastener straps 232. Straps 228 are positioned over the shoulders and secured to each other by clip or buckle 234. Straps 232 are positioned about the abdomen area and secured to each other by clip or buckle 236. Clips 234, 236 are configured to permit securing and unsecuring of fastener straps 228, 232, and thus, flexible substrate 202 to the patient. Any means for coupling fastener straps 228, 232 to respective apertures 226, 230 is envisioned, e.g., Velcro fasteners, clips, latches In another embodiment of sensor array apparatus 100 shown in FIG. 2B, upper and lower segments 208, 210 may be elongated such that their respective ends 214,216 extend over the shoulder/neck area and the abdomen of the patient. With this arrangement, respective ends 214,216 of upper and lower segments 208, 210 may be secured with buckles, clasps, clips or other suitable fastening means to secure sensor array apparatus 100 to the patient.

Flexible substrate 202 may also be formed with multiple materials with or without elongation properties. Creation of elongation zones would enable some portions of flexible substrate 202 to stretch, such as upper and lower segments 208, 210, while sections without elongation properties would maintain in a fixed relationship to each other. In FIG. 2A, for example, flexible substrate 202 may include an elongation zone 238 positioned between electrodes E5 and E6 on lower segment 210. Similarly, upper segment 208 may include elongation zones 240, 242 respectively. Elongation zones 238, 240, 242 of flexible substrate 202 may be, for example, a continuous serpentine pattern and/or stretchable cloth-based material suitable for expansion/retraction upon application of flexible substrate 202 to the patient to accommodate body types of varying size/height. With this arrangement, placement on the torso may be accomplished by utilizing an electrode placement template. The electrode placement template details the desired arrangement of the electrode array. Thus, when placed on the torso, electrode placement locations may be marked on the patient's skin with the use of the template. Each marked location is a predetermined distance along the skin relative to the placement marker. The marked locations for each electrode are a predetermined distance from the marked location for the placement marker. The flexible substrate is elongated and placed on the torso such that each electrode is positioned on the marked locations. Multiple templates may ensure proper placement on various sized patients.

With a flexible substrate 202 incorporating elongation characteristics, means may be provided for preventing conductive traces 220 from breaking when flexible substrate 202 is elongated. Such means may include incorporating a zigzag pattern (e.g., accordion-structure or bellows) within conductive traces 220, which straightens when flexible substrate 202 is elongated. Alternatively, portions of flexible substrate 202 and corresponding traces 220 may be folded over such that the folded section provides additional length when the substrate is elongated. As a further alternative, conductive traces 220 may be formed of a material such as gold which exhibits a limited range of stretching or elongation.

Flexible substrate 202 also may be formed of material with an elastic memory. With an elastic memory material, flexible substrate 202 will remain under tension when elongated, but, is biased to return to its original shape. Placing flexible substrate 202 under constant tension would enable the measurement of tension changes due to physical movements of the torso by the placement of a strain gauge device on the flexible substrate 202. Flexible substrate 202 may also be formed with materials without elastic memory. Materials without elastic memory exhibit elongation properties but once elongated, remain elongated and do not attempt to return to the original shape and length.

Figure 4:
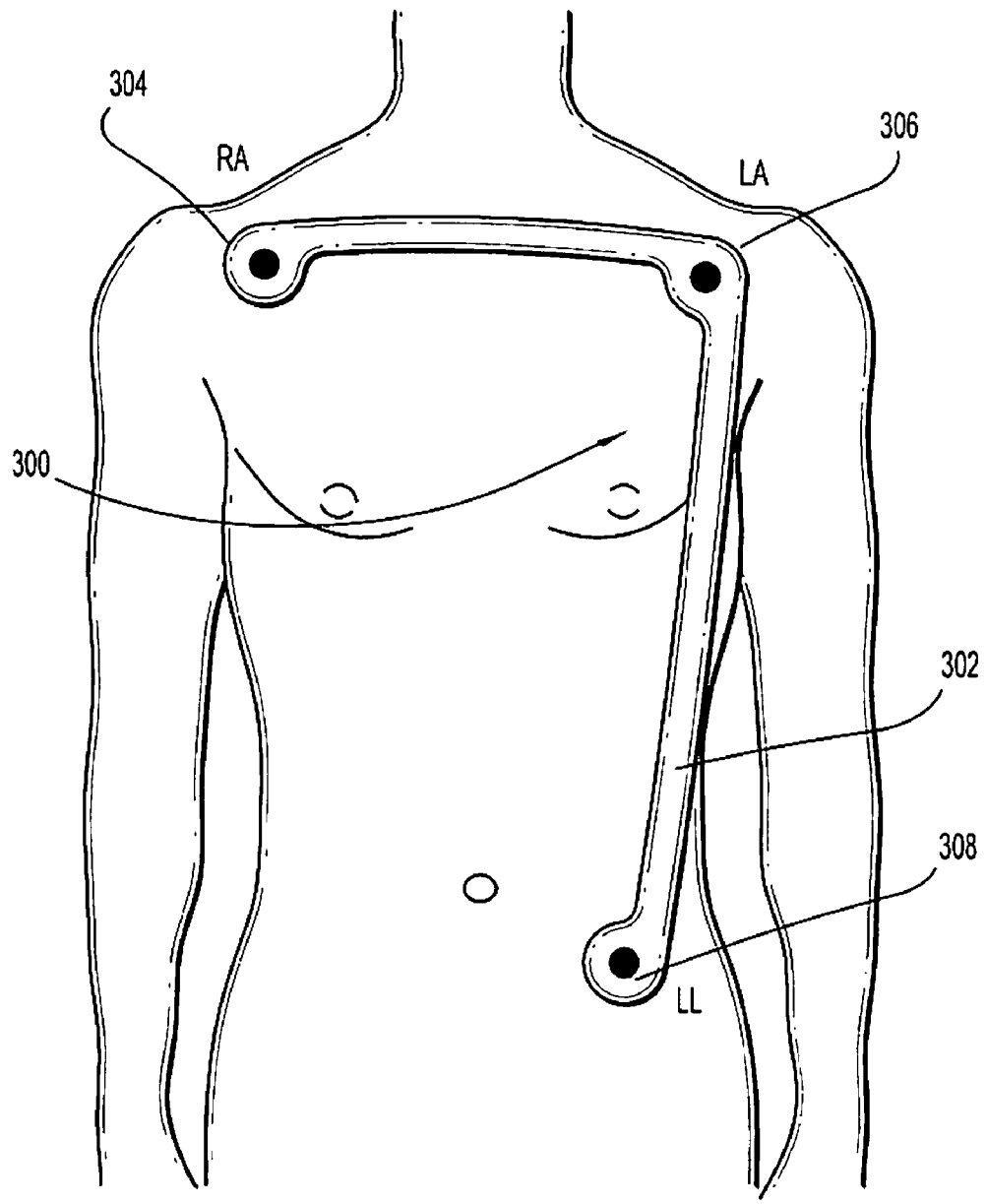
FIGS. 4-7 illustrate alternate embodiments of the sensor array apparatus.

FIG. 4 illustrates an alternate embodiment where sensor array apparatus is adapted for use as a three lead ECG set. Sensor array apparatus 300 includes an asymmetrical flexible substrate 302 and three electrode leads 304, 306, 308 which correspond to the RA, LA and LL electrode leads respectively. Substrate 302 and the electrodes may be integrated via any of the manners discussed hereinabove. Furthermore, any of the aforementioned means for securing sensor array apparatus 300 to the subject, e.g., straps, etc are envisioned.

Figure 5:
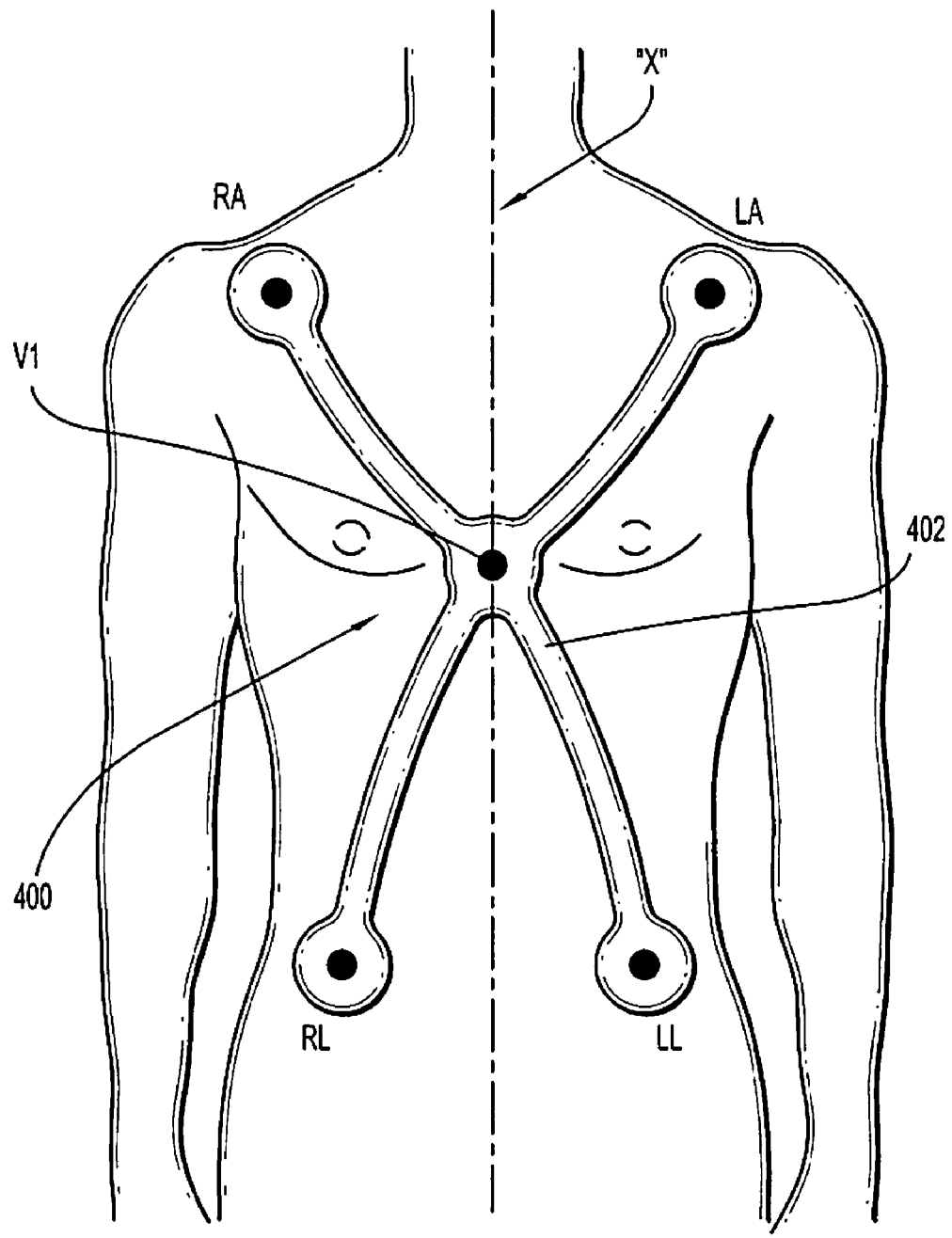

FIG. 5 illustrates an alternate embodiment of the present disclosure. Sensor array apparatus 400 is adapted for use in a five lead ECG set having substrate 402 which is symmetrical relative to central axis "x" and electrode leads V1, RA, LA, RL, LL integrated into the substrate 402.

Figure 6:
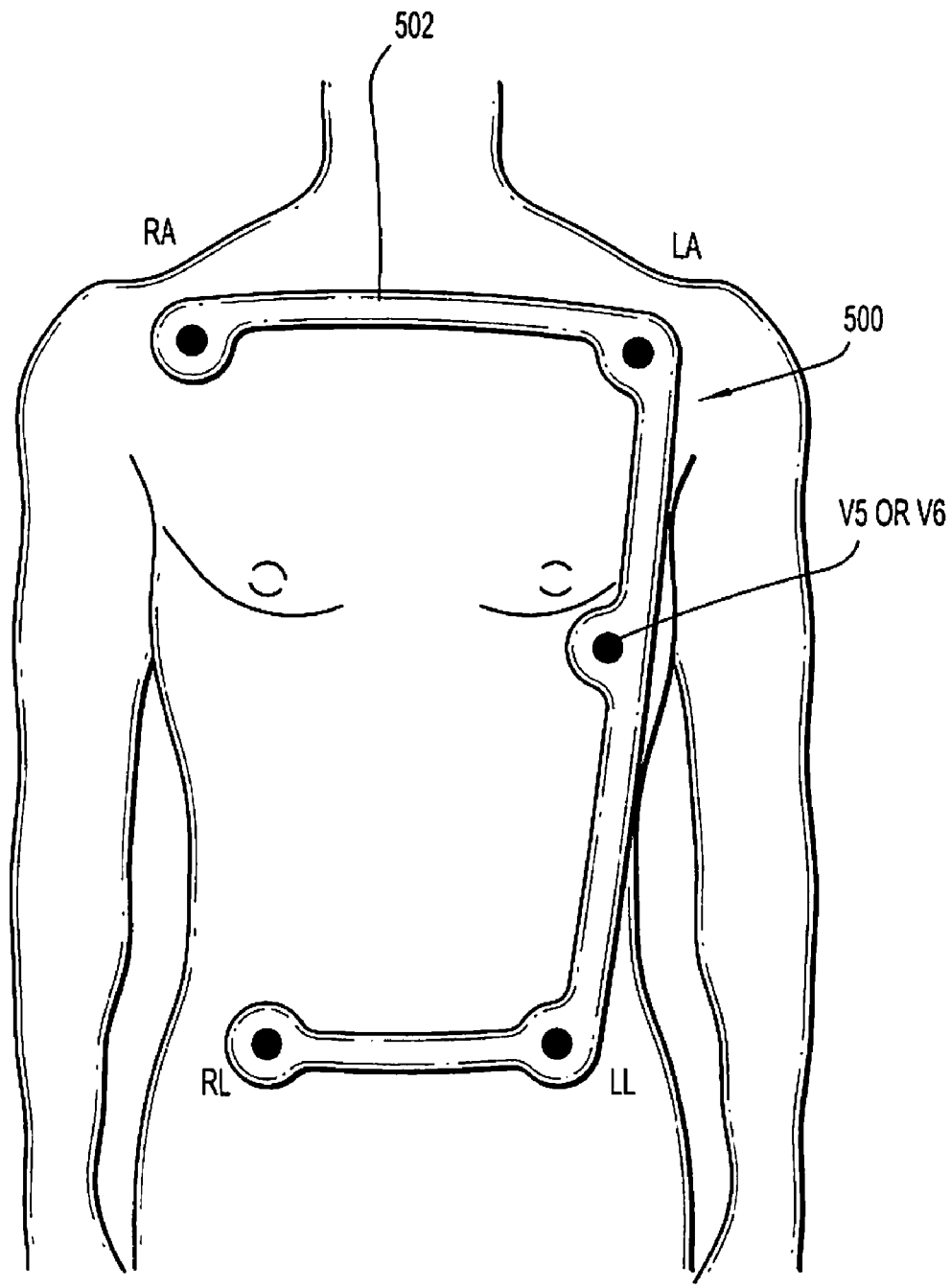

FIG. 6 illustrates an alternate sensor array apparatus 500 adapted for use as a five ECG lead set where substrate defines a c-shaped configuration 502 and has electrode leads RA, LA, RL and LL integrated therein. This sensor array apparatus 500 may have application in open heart surgery. With this arrangement, the V5, V6 leads may be used in lieu of the V1 lead to obtain the desired biomedical signals.

Figure 7:
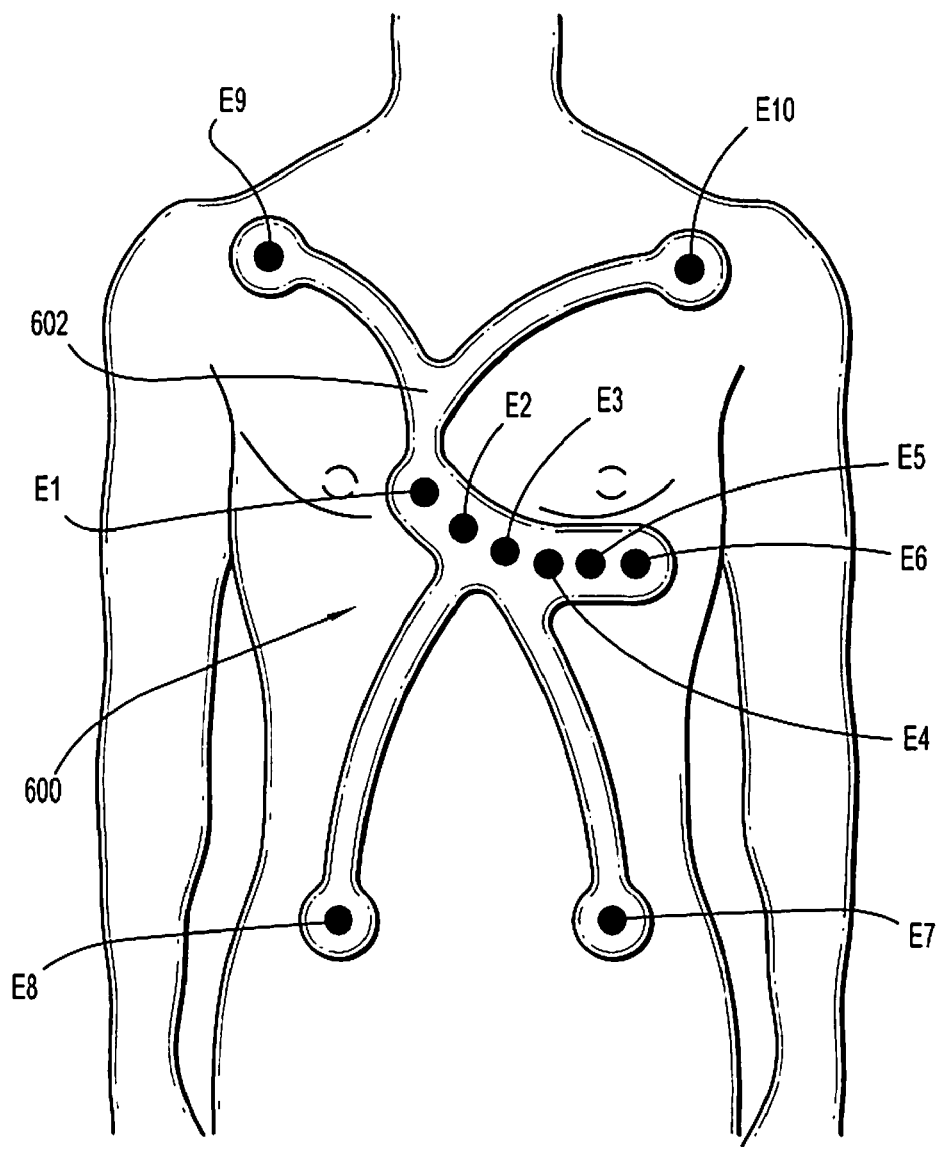

FIG. 7 illustrates another embodiment of the sensor array apparatus 600. Sensor array apparatus 600 is adapted for use as a 12 lead ECG set in a manner similar to that discussed hereinabove in connection with the embodiment of FIGS. 1-3. Sensor array apparatus 600 includes an asymmetrical flexible substrate 602 having a shape as illustrated in FIG. 7. Substrates 602 has electrodes E1-E10 integrated therein and positioned at the appropriate predetermined locations when applied to the patients. Means for securing sensor array apparatus 600 to the patient may include any of the aforementioned methodologies hereinabove discussed.

It is to be understood that the foregoing description is merely a disclosure of particular embodiments and is in no way intended to limit the scope of the disclosure. It is further envisioned that the sensor apparatus may incorporate color coding to correspond to industry standards set forth by AHA, AHMI, IEC to assist in application of the apparatus during the ECG procedure. Written indices or instructions may be incorporated into the illustration setting forth a protocol for use and application of the substrate. Other possible modifications will be apparent to those skilled in the art and are intended to be within the scope of the present disclosure.

What is claimed is:

1. A sensor array apparatus for monitoring medical signals, which comprises:

a flexible substrate adapted for positioning relative to the torso of a patient, the flexible substrate including a central segment defining a central axis and adapted to generally conform to an area extending along the sternum of the patient, an upper segment extending at least to the central segment and adapted to generally conform to the chest area of the patient, and a lower segment extending bilaterally outwardly from the central segment, and an intermediate segment extending bilaterally outwardly from the central segment between the upper and lower segments;

at least one medical electrode disposed on each of the segments, wherein more than one medical electrode is disposed on the lower segment on a common side of the central axis; and a connector in electrical communication with the medical electrodes and adapted to connect to an electronic monitoring system.

2. The sensor array apparatus according to claim 1 wherein each of the upper segment and the lower segment is adapted to releasably couple to at least one fastener strap.

3. The sensor array apparatus according to claim 1 including a first pair of fastener straps releasably coupled to a first end of each of the upper segment and the lower segment and adapted to releasably couple to a corresponding second pair of fastener straps releasably coupled to a corresponding second end of each of the upper segment and the lower segment.

4. The sensor array apparatus according to claim 3 wherein the fastener straps releasably coupled to the upper segment are adapted to at least partially circumscribe the neck area of the patient to releasably couple to each other generally about the upper back area of the patient and the fastener straps releasably coupled to the lower segment are adapted to at least partially circumscribe the abdominal area of the patient to releasably couple to each other generally about the lower back area of the patient.

5. The sensor array apparatus according to claim 1 including at least one reference electrode disposed on the central segment of the flexible substrate for positioning of the substrate relative to a specific location on the patient.

6. The sensor array apparatus according to claim 5 wherein the reference electrode is generally aligned with respect to the central axis.

7. The sensor array apparatus according to claim 6 wherein the medical electrodes disposed on the segments are a predetermined distance relative to the reference electrode when the flexible substrate is applied to the patient, whereby the predetermined distance for at least some of the medical electrodes is substantially the same.

8. The sensor array apparatus of claim 5 wherein the flexible substrate is generally symmetrically arranged about the central axis whereby each of the upper, central, and lower segments include at least one medical electrode disposed thereon on each side of the central axis.

9. The sensor array apparatus of claim 5 wherein the medical electrodes disposed on respective segments on each side of the central axis are spaced at substantially equal distances relative to the reference electrode when the flexible substrate is positioned relative to the patient.

10. The sensor array apparatus of claim 1 wherein at least one of the upper, central, and lower segments include properties of elongation.

11. The sensor array apparatus of claim 1 wherein the flexible substrate is a dielectric.

12. The sensor array apparatus of claim 1 wherein the flexible substrate is formed of material having an elastic memory.

13. The sensor array apparatus of claim 1 wherein the medical electrodes are disposed on the flexible substrate, wherein conductive traces disposed on the flexible substrate connect the medical electrodes to the connector.

14. The sensor array apparatus of claim 13 wherein the conductive traces are disposed on the flexible substrate by a silk screen printing process, photoengraving process, chemical etching process, laser etching process, or masking process.

15. The sensor array apparatus of claim 1 wherein a first end of the upper segment is adapted to releasably couple to a corresponding second end of the upper segment generally about the upper back area of the patient and a first end of the lower segment is adapted to releasably couple to a corresponding second end of the lower segment generally about the lower back area of the patient.

16. A sensor array apparatus for monitoring medical signals, which comprises:

a flexible substrate adapted for positioning relative to the torso of a patient, the flexible substrate including a central segment arranged about a central axis and adapted to generally conform to an area extending along the sternum of a patient, an upper segment extending bilaterally outwardly from the central segment and adapted to generally conform to the chest area of a patient, a lower segment extending bilaterally outwardly from the central segment and adapted to generally conform to the abdominal area of the patient, and an intermediate segment extending bilaterally outwardly from the central segment between the upper and lower segments, wherein at least one of the upper segment and the lower segment is adapted to releasably couple to at least one fastener strap adapted to secure the flexible substrate to the torso of the patient;

at least one medical electrode disposed on each of the segments, wherein more than one medical electrode is disposed on the lower segment on a common side of the central axis; and a connector in electrical communication with the medical electrodes and adapted to connect to an electronic monitoring system.

17. The sensor array apparatus according to claim 16 including at least one reference electrode disposed on the central segment of the flexible substrate and generally aligned with respect to the central axis for positioning of the substrate relative to a specific location on the patient.

18. A sensor array apparatus for monitoring medical signals, which comprises:

a flexible substrate adapted for positioning relative to the torso of a patient, the flexible substrate including an upper substantially horizontal segment, a lower substantially horizontal segment, an intermediate substantially horizontal segment disposed between the upper and lower segments, and at least one substantially vertical segment, the lower substantially horizontal segment extending bilaterally outwardly from the at least one substantially vertical segment, wherein at least one of the substantially horizontal segments and the substantially vertical segment are adapted to releasably couple to at least one fastener strap adapted to secure the flexible substrate to the torso of the patient;

at least one medical electrode disposed on each of the segments, wherein more than one medical electrode is disposed on the lower substantially horizontal segment on a common side of the at least one substantially vertical segment; and a connector in electrical communication with the medical electrodes and adapted to connect to an electronic monitoring system.

19. The sensor array apparatus of claim 18, wherein the flexible substrate is asymmetrical.

20. The sensor array apparatus of claim 19, wherein the sensor array apparatus is adapted for use as a three lead ECG set.

21. The sensor array apparatus of claim 18, wherein the sensor array apparatus is adapted for use as a five lead ECG set.

22. The sensor array apparatus of claim 18, wherein the sensor array apparatus is adapted for use as a twelve lead ECG set.

* * * * *